(12) United States Patent
Loria

(10) Patent No.: US 9,993,578 B1
(45) Date of Patent: Jun. 12, 2018

(54) SILICONE OIL-IN-WATER COMPOSITION USEFUL AS AN INJECTABLE FILLER AND AS A SCAFFOLD FOR COLLAGEN GROWTH

(71) Applicant: Lorstan Pharmaceutical, LLC, Doral, FL (US)

(72) Inventor: Victor Loria, Miami, FL (US)

(73) Assignee: Lorstan Pharmaceutical, LLC, Doral, FL (US)

( * ) Notice: Subject to any disclaimer, the term of this patent is extended or adjusted under 35 U.S.C. 154(b) by 0 days. days.

(21) Appl. No.: 15/405,240

(22) Filed: Jan. 12, 2017

(51) Int. Cl.
*A61L 27/18* (2006.01)
*A61L 27/58* (2006.01)
*A61L 27/26* (2006.01)

(52) U.S. Cl.
CPC ............... *A61L 27/18* (2013.01); *A61L 27/26* (2013.01); *A61L 27/58* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 4,496,687 A | 1/1985 | Okada et al. | |
| 4,960,764 A | 10/1990 | Figueroa, Jr. et al. | |
| 5,300,286 A | 4/1994 | Gee | |
| 2009/0169615 A1* | 7/2009 | Pinsky | A61K 8/14 424/450 |
| 2010/0268189 A1* | 10/2010 | Byrnes | A61M 37/00 604/506 |
| 2012/0189588 A1* | 7/2012 | Nahas | A61K 31/00 424/93.7 |
| 2014/0079686 A1 | 3/2014 | Barman et al. | |
| 2016/0354516 A1 | 12/2016 | Chuang | |

OTHER PUBLICATIONS

Chasan, P.E. (2007). "The History of Injectable Silicone Fluids for Soft-Tissue Augmentation." Plastic and Reconstructive Surgery 120(7): pp. 2034-2040.

El-Hamouz et al. (2009). "Dispersion of silicone oil in water surfactant solution: effect of impeller speed, oil viscosity and addition point on drop size distribution." Chemical Engineering and Processing: Process Intensification 48.2: pp. 633-642.
Fulton et al. (2012). "The optimal filler: immediate and long-term results with emulsified silicone (1,000 centistokes) with cross-linked hyaluronic acid." Journal of drugs in dermatology: JDD 11.11: pp. 1336-1341.
Jones, D. H. (2009). "Semipermanent and permanent injectable fillers." Dermatologic clinics 27.4: pp. 433-444.
Sasidaran et al. (2012). "Low-grade liquid silicone injections as a penile enhancement procedure: Is bigger better?." Urology annals 4.3: pp. 181-186.
Vaziri et al. (2016). "Tamponade in the surgical management of retinal detachment." Clinical ophthalmology (Auckland, NZ) 10: pp. 471-476.
Yang et al. (2012). "Tolerability and efficacy of newly developed penile injection of cross-linked dextran and polymethylmethacrylate mixture on penile enhancement: 6 months follow-up." International journal of impotence research 25.3: pp. 99-103.
Wollina et al. (2015). Fillers for the improvement in acne scars. Clinical, cosmetic and investigational dermatology, 8, 493-499.
International Search Report from corresponding PCT/US2018/013512 dated Mar. 29, 2018.

* cited by examiner

*Primary Examiner* — Robert A Wax
*Assistant Examiner* — Randeep Singh
(74) *Attorney, Agent, or Firm* — Caesar Rivise, PC

(57) ABSTRACT

The present invention relates to compositions in the form of oil-in-water dispersions comprising a silicone oil having an average droplet diameter from about 30 microns to about 2000 microns and a polymeric thickening agent. These compositions are useful for stimulating collagen production in human patients and other mammals, and have applications for soft tissue augmentation for various medical and cosmetic procedures. The present invention also relates to methods for preparing these compositions and to methods for stimulating collagen production in human patients and other mammals in need thereof. In contrast to the prior art, the compositions and methods of the present invention are particularly useful for stimulating the production of high quality collagen that is uniform, smooth, long-lasting, and having good structural integrity.

26 Claims, No Drawings

SILICONE OIL-IN-WATER COMPOSITION USEFUL AS AN INJECTABLE FILLER AND AS A SCAFFOLD FOR COLLAGEN GROWTH

BACKGROUND OF THE INVENTION

1. Field of Invention

This invention relates to compositions comprising silicone oil-in-water emulsions and to methods of making and using such compositions as a dermal filler.

2. Description of Related Art

There has been a longstanding need, both medical and cosmetic, to develop materials and methods for soft tissue augmentation. The need or desire for this augmentation can vary, and can include, for example: the treatment of facial fine lines, wrinkles, and scars (such as acne scars), the reconstruction of soft-tissue that has been damaged due to trauma (such as a hernia repair) or disease; the promotion of wound healing and tissue regeneration; the augmentation of breast tissue; and the enhancement of the male genitalia. A number of materials and treatment techniques for soft tissue augmentation have been available at least since the mid-1900s. However, many of these materials and techniques have disadvantages associated with them.

Examples of treatment techniques include reconstructive surgery, implantation of prosthetics, and the injection of various materials. Surgical intervention can be used to repair or reconstruct tissue and can involve an autograft, where tissue is taken from one part of the patient's own body and transplanted into another; or an allograft, where the tissue is obtained from a non-identical donor. For example, allografts of human cadaver bone are often employed in dental procedures involving jaw bone augmentation. Surgical intervention can also be used to reconstruct tissue and for the placement of implants and prosthetics. Examples of implants and prosthetics include those made from synthetic materials such as silicone, polyethylene, and polytetrafluoroethylene (an example of which is Gore-Tex), and those from naturally derived materials such as acellular dermal matrix (also known as "ADM"), collagen, cadaver bone, and tissue parts from animal sources, such as porcine and bovine heart valves.

In addition to surgical techniques, injection techniques employing needles or cannulas of various diameters have been used to inject patients with materials such as silicone oil, collagen, hyaluronic acid (an anionic, nonsulfated glycosaminoglycan distributed widely throughout connective, epithelial, and neural tissues), autologous fat (fat obtained from the same individual), calcium hydroxyapatite, poly-L-lactic acid, poly(methyl methacrylate), and botulinum toxin type A Botox. It is recognized that Botox injections are not technically used to augment tissue, but rather to provide their effects by blocking signals from the nerves to the muscles, which can help facial wrinkles to relax and soften. See for example, Jones, D., Semipermanent and Permanent Injectable Fillers, Dermatol Clin 27 (2009) 433-444. However, these materials each have their own specific properties, longevity of treatment, and side effects. Some materials, such as collagen and autologous fat, tend to be temporary and are resorbed and require repeated treatments at regular intervals. Other treatments, such as silicone oil, tend to be more permanent and do not break down as readily. Also, materials such as silicone oils appear to stimulate the production of the patient's own collagen, further adding to a greater and more natural tissue augmentation volume, filling, and permanence effect. Dermal fillers such as cross-linked dextran and poly(methyl methacrylate) (PMMA) have been reported. However, information seems to be lacking on the long-term effectiveness of this material for penile enhancement. See Yang, Y. et al., Tolerability and Efficacy of Newly Developed Penile Injection of Cross-linked Dextran and Polymethyacrylate Mixture on Penile Enhancement, Int. J. Import. Res., 2013, 25(3), 99-103.

In the present invention it has been realized that for effective soft tissue augmentation it would be highly desirable to stimulate the production of high quality collagen. Collagen is the main structural protein in the extracellular space in the various connective tissues in humans and animals. As the main component of connective tissue, it is the most abundant protein in mammals, making up from about 25% to 35% of the whole-body protein content. Depending upon the degree of mineralization, collagen tissue can be compliant or rigid. A single collagen molecule, also referred to as tropocollagen, is the component used to make up larger collagen aggregates, such as fibrils. These aggregates are arranged in different combinations and concentrations to provide varying tissue properties.

Depending on the area of the human body to be treated, it would be highly desirable to stimulate the generation of new collagen that is preferentially produced and laid down as uniform, smooth sheets. The generation of such uniform and smooth collagen would be especially desirable in highly visible or sensitive areas of the body, such as the face, breasts, or male genitalia. In other cases, such as for surgical reconstruction and wound healing applications, structural integrity and tensile strength are important characteristics. A particular instance in which these structural and strength properties are important is for hernia repair, where the repair is subject to a great deal of constant mechanical stress. Therefore, it would also be highly desirable to provide compositions and methods for carefully controlling the quantity, structure, and quality of the collagen produced, depending on the application and outcome sought.

Certain types of silicone oils, when appropriately delivered, can potentially stimulate the production of collagen. However, to generate appropriate collagen production, the physician or practitioner cannot simply place or inject a silicone oil into the target tissue of the patient.

The development of silicone oils and their use in medical and cosmetic procedures has a long and complicated history. See for example, Chasan, P., The History of Injectable Silicone Fluids for Soft-Tissue Augmentation, Plastic and Reconstructive Surgery, Volume 120, Number 7, pp. 2034-2040, December 2007. The first polydimethylsiloxanes were synthesized in the 1930s. Polydimethylsiloxanes can generally be described by the chemical formula, $CH_3[Si(CH_3)_2O]_nSi(CH_3)_3$, where n is the number of repeating monomer $[SiO(CH_3)_2]$ units. Polydimethylsiloxanes have many industrial applications, including their use as lubricants, antifoaming agents, and hydraulic fluids. In recent years, silicone oils found their way into personal care products such as hair and skin conditioners because of their substantive properties and smooth feel. See, e.g., U.S. Pat. Nos. 4,960,764 and 5,300,286.

The earliest use of silicones for tissue augmentation goes back to at least the time of the second World War II when some women in Japan had silicone oil injections to augment their bustlines. The more controlled, medical use of injected silicones goes back to 1965 when Dow Corning obtained approval for investigation of its silicone oil, MDX 4-4011, in patients, for indications including the treatment of wrinkles and acne scars. Other studies were conducted on silicone oils for tissue augmentation. However, there is a paucity of rigorous scientific data, and reports of various adverse reactions have been reported. Such adverse reactions include scarring, granuloma and nodule formation, inflammation, and migration or pooling of the silicone oil to and in the extremities, such as the legs. Granuloma formation is an inflammatory response, wherein the immune system attempts to wall off substances it perceives as foreign but is unable to eliminate them. From many of the studies it is difficult to determine whether the silicone oil itself, possible contaminants or adulterants therein, the injection technique, or the quantity of silicone oil used was/were responsible for the adverse effects. Silicone oils, however, have, found successful use in ophthalmology as intraocular tamponades (i.e., as plugs or tampons) for treating retinal detachments. See for example, Vaziri, K. et al., Tamponade in the surgical management of retinal detachment, Clinical Ophthalmology 2016:10, pp. 471-476.

In order to minimize adverse reactions with the use of silicone oil injections for soft tissue augmentation, efforts have been made to use more highly purified silicone oils and to minimize the injection amounts in any given tissue area. Currently, silicone oil is used clinically for soft tissue augmentation of the lips and nasolabial folds and to correct irregularities in the cheek and nose.

The literature reports a microdroplet technique, in which very small amounts (0.01 ml to 0.03 ml) of silicone oil are injected subcutis at intervals of 2 to 10 mm apart in the desired body site with a serial puncture technique, or up to about 1 ml is injected by a tunneling or fanning technique. However, the precise injection of small quantities of silicone oil can be tedious and the end result highly dependent on the skill and judgment of the practitioner. Also, there are reports of the use of this technique for male enhancement. See, for example Urol. Ann. 2012 September-December; 4(3): 181-186.doi: 10.4103/0974-7796.102672 PMCID: PMC3519113. Low-grade liquid silicone injections as a penile enhancement procedure: Is bigger better? Ramesh Sasidaran, Mohd Ali Mat Zain, and Normala Hj Basiron. Even in these instances, the quantities of injected silicone oil per injection site are still relatively large and it can be difficult to achieve the uniformity desired for high quality collagen stimulation and production, thus resulting in a bumpy nodular pattern, which would be highly undesirable in the penile area. In addition, it would be contraindicated to inject the penile skin with a microdroplet technique because of the subcutaneous space and the very thin dermis.

A further complication is added to the challenges associated with silicone injections, because of phagocytosis, whereby foreign materials are removed by the body's immune system, i.e., the phagocytes. Therefore, if the silicone droplets are too small in size, i.e., under about 30 microns in diameter, the silicone oil would likely not be effective, as the phagocytes would phagocytize or engulf the silicone oil before collagen production could be stimulated. Therefore, the delivery of the appropriate type of silicone oil, of the correct droplet size range, and with the appropriate distribution and residence time, can all be important factors for the stimulation of effective collagen production.

Fulton et al. "The optimal filler: immediate and long-term results with emulsified silicone (1,000 centistokes) with cross-linked hyaluronic acid." Journal of drugs in dermatology: JDD 11.11 (2012): 1336-1341 discloses the use of silicone oil-in-water emulsions containing hyaluronic acid as injectable fillers for facial implantation.

Despite the foregoing developments, there is a need for the development of safe and effective compositions and methods for providing permanent soft tissue augmentation, and particularly for augmentation of more delicate and challenging sites such as the male genitalia. Preferably, these compositions and methods would provide a means for stimulating the targeted tissue to produce sufficient quantities of high-quality collagen to permanently achieve the desired result.

All references cited herein are incorporated herein by reference in their entireties.

BRIEF SUMMARY OF THE INVENTION

A first aspect of the invention relates to a filler composition comprising: (a) 1% to 80% of a silicone oil having a viscosity from 1500-30000 centistokes (cSt); (b) 20% to 99% of water; and (c) 0.005% to 10% of a thickening agent, wherein the filler composition is a pharmaceutically acceptable oil-in-water emulsion, the silicone oil is dispersed in the water as droplets having an average diameter from 30 microns to 2000 microns and the thickening agent is sufficiently biodegradable when implanted subcutaneously in a human to provide a temporary scaffold for collagen growth between silicone oil droplets.

In certain embodiments of the filler composition, the thickening agent when implanted subcutaneously is sufficiently biodegradable such that the temporary scaffold dissolves in 14-28 days.

In certain embodiments of the filler composition, the average diameter of the droplets is greater than 100 microns.

In certain embodiments of the filler composition, the thickening agent is a member selected from the group consisting of carboxymethyl cellulose, poly(ethylene oxide), poly(propylene oxide), collagen and mixtures thereof.

In certain embodiments of the filler composition, the thickening agent is carboxymethyl cellulose.

In certain embodiments of the filler composition, the thickening agent is carboxymethyl cellulose or hyaluronic acid, and the thickening agent is cross-linked with 1,4-butanediol diglycidyl ether in an amount from 0.05% to 7% based on a weight of the thickening agent.

In certain embodiments of the filler composition, the thickening agent is hyaluronic acid cross-linked with a degree of modification of 0.1 to 0.9.

In certain embodiments of the filler composition, the filler composition has a viscosity of 1500 cSt to 20,000,000 cSt.

In certain embodiments of the filler composition, the silicone oil comprises at least one member selected from the group consisting of polydimethylsiloxane, fluorinated polysiloxanes, dimethiconol and silicone polyethers.

In certain embodiments of the filler composition, the silicone oil comprises polydimethylsiloxane with a viscosity of 5000 cSt.

In certain embodiments of the filler composition, the silicone oil constitutes 20% to 50% of the filler composition.

In certain embodiments of the filler composition, the water constitutes 50% to 80% of the filler composition.

In certain embodiments of the filler composition, the thickening agent constitutes 0.01% to 1% of the filler composition.

In certain embodiments, the filler composition further comprises at least one ion selected from the group consisting of: up to 154 mmol/L of sodium ion; up to 154 mmol/L of chloride ion; up to 28 mmol/L of lactate ion; up to 4 mmol/L of potassium ion; and up to 1.5 mmol/L of calcium ion.

In certain embodiments, the filler composition is effective to stimulate formation of a collagen matrix which anchors the silicone oil droplets in place as the temporary scaffold dissolves.

A second aspect of the invention is directed to a method for preparing a filler composition of the invention, which comprises the steps of:

(i) preparing a silicone oil phase comprising the steps of: (a) providing a silicone oil that is substantially sterile and substantially free of pyrogen; (b) mixing the silicone oil with 1-5 volumes of sterile injectable water for 4 to 6 minutes at 1200 to 1500 rpm; (c) allowing the silicone oil and water mixture to separate into a lower water layer and an upper silicone layer; (d) removing the lower water layer and collecting the upper silicone layer; and (e) repeating steps (b) through (d) on the silicone oil at least once to obtain the silicone oil phase;

(ii) preparing a thickened water phase solution comprising the steps of: (a) dissolving with stirring a thickening agent in a sterile solvent selected from the group consisting of injectable water, normal saline, Ringer's solution, and lactated Ringer's solution, to form a thickened water phase solution; (b) sterilizing the thickened water phase solution; and (c) optionally freezing and thawing the sterilized thickened water phase solution; and (iii) preparing a silicone oil-in-water emulsion by combining 35-45 parts by volume of the silicone oil phase with 55-65 parts by volume of the thickened water phase solution with agitation to form an emulsion of the silicone oil within the water.

In certain embodiments of the preparation method, the sterile solvent contains a cross-linking agent which forms cross-links in the thickening agent.

In certain embodiments of the preparation method, the cross-linking agent is 1,4-butanediol diglycidyl ether in an amount from 0.05% to 7% based on a weight of the thickening agent.

A third aspect of the invention is directed to a soft tissue augmentation method comprising subcutaneously injecting into a patient a filler composition of the invention.

In certain embodiments of the soft tissue augmentation method, a volume of 20 to 60 ml is injected into a single injection site.

In certain embodiments of the soft tissue augmentation method, the filler composition stimulates collagen growth; the thickening agent forms a temporary scaffold for collagen growth between silicone oil droplets; and a collagen matrix anchors the silicone oil droplets in place as the temporary scaffold dissolves within 14-28 days.

In certain embodiments of the soft tissue augmentation method, the filler composition is injected into a penis or a scrotum for penis or scrotum enhancement.

In certain embodiments of the soft tissue augmentation method, a wrinkle or depression on the face or body is filled with the filler composition.

In certain embodiments of the soft tissue augmentation method, a scar is repaired.

In certain embodiments of the soft tissue augmentation method, a hernia is repaired.

In certain embodiments of the soft tissue augmentation method, the filler composition is injected into a breast for breast enhancement.

These and other aspects of the invention will become apparent from the disclosure herein.

DETAILED DESCRIPTION OF PREFERRED EMBODIMENTS OF THE INVENTION

The inventor has surprisingly found that the compositions and methods of the present invention are useful for stimulating collagen growth and providing a temporary scaffold for the growth of a collagen matrix between silicone oil droplets. Unlike the prior art, the compositions and methods of the present invention are particularly useful for filling soft tissue in a manner that is uniform, smooth, long-lasting, and has good structural integrity. The invention is useful for soft tissue augmentation, soft tissue repair and/or scar reduction repair, and is especially well-suited for penis enlargement and scrotal enlargement.

Definitions

The term "dispersion" means a system in which small particles or droplets are distributed or "dispersed" in a continuous phase, such as water. A dispersion can be classified in different ways, including particle size, whether or not precipitation occurs, and the presence of Brownian motion. A common example of a dispersion is a water-based ink. In the present invention the compositions are generally silicone oils dispersed in an aqueous phase, which can be referred to as a silicone oil-in-water emulsion.

The term "emulsion" as used herein means a mixture of two or more liquids that are normally immiscible. Emulsions are part of a more general class of two-phase systems that are called colloids. An example of an emulsion is an oil-in-water ("o/w") emulsion in which the oil phase is dispersed in the continuous water phase. A common example of an emulsion is milk. In the present invention the compositions can also be in the form of oil-in-water emulsions wherein the oil phase is a silicone oil (i.e., a "silicone oil-in-water emulsion").

The term "viscosity" is used herein in its standard sense as a measure of the resistance of a fluid to gradual deformation by shear stress or tensile stress. The term is used in a more informal manner as the concept of the thickness of a fluid. The viscosity of a fluid can be reported as the dynamic, i.e., the absolute, viscosity or the kinematic viscosity. The dynamic viscosity of a fluid is typically reported in centiStokes (cSt) and relates to the resistance of the fluid to shearing flows, where adjacent layers move parallel to each other with different speeds. The kinematic viscosity of a fluid is typically reported in centipoise (cP) and is the ratio of the dynamic viscosity to the density of the fluid. For example, a silicone fluid having a dynamic viscosity of 1000 cSt and a density of 0.90 g/ml would have a kinematic viscosity of 1111.11 cP [which is 1000 cSt divided by 0.90 g/ml].

As used herein, use of the expression "pharmaceutically acceptable" to describe a material means that the material is suitable for use in contact with the tissues of humans and lower animals without undue toxicity, incompatibility, instability, irritation, allergic response and the like, commensurate with a reasonable benefit/risk ratio.

As used herein, use of the term "biodegradable" to describe a material means that the material is degraded when implanted in a host human or lower animal.

All percentages and ratios used herein, unless otherwise indicated, are by weight. It is also recognized that in certain instances it is useful and convenient to describe the compositions on a volume basis.

The invention can be embodied in other specific forms without departing from the spirit or essential characteristics thereof. The foregoing embodiments are to be considered in all respects illustrative rather than limiting on the invention described herein. In the various embodiments of the present invention, such as for example, the compositions and methods of the present invention, where the term comprises is used, it is also contemplated in other embodiments that the present; invention consists essentially of, or consists of, the embodiments. Further, it should be understood that the order of steps or order for performing certain actions is immaterial so long as the invention remains operable. Moreover, two or more steps or actions can be conducted simultaneously in some instances.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as being composed of the components prior to mixing, because upon mixing certain components can further react or be transformed into additional materials.

Compositions of the Invention

The compositions of the invention are particularly useful as soft tissue fillers which stimulate the production of high quality collagen that is uniform, smooth, long-lasting, and has good structural integrity. The compositions comprise silicone oil, water and a thickening agent.

Silicone Oil

Liquid injectable silicone (LIS) has been used as a soft tissue filler for an array of cutaneous and subcutaneous atrophies. It is distinctive among the soft tissue augmenting agents with regard to its relative permanence, versatility, and cost-to-benefit ratio. Yet, liquid silicone can also be distinguished as one of the least forgiving fillers, requiring extensive experience and precise injection techniques in order to achieve optimal results.

The silicone oils useful herein for stimulating collagen production are selected from polydimethylsiloxanes, fluorinated polysiloxanes, dimethiconol, silicone polyethers, and mixtures thereof. Polydimethylsiloxanes, also known as dimethicones, can generally be described by the chemical formula, $CH_3[Si(CH_3)_2O]_nSi(CH_3)_3$, where n is the number of repeating monomer $[SiO(CH_3)_2]$ units.

The compositions of the present invention comprise from about 1% to about 80%, in other embodiments from about 5% to about 60%, and in further embodiments from about 20% to about 50% by weight of a silicone oil.

The silicone oil should generally have a viscosity greater than 1000 centistokes (cSt). Preferably, the silicon oil viscosity is 1,500-30,000 cSt or 5,000-20,000 cSt. These are dynamic viscosity ranges and can be converted to the corresponding kinematic viscosity ranges by dividing by the density of the particular silicone oil.

Examples of silicone oils particularly useful herein include polydimethylsiloxanes, which are generally classified with the CAS identification number 63148-62-9. Some commercially available polydimethylsiloxanes include the following materials.

ADATO Sil-Ol-Silicone Oil, also known as ADATO SIL-OL 5000—Product Code ES-50005 is available form Bausch & Lomb, Rochester, N.Y. 14609. The material is described as a clear oily liquid with a viscosity of 5000 to 5900 centipoise (cP) at 25° C. and a specific gravity (density to water) of 0.913 at 25° C. A silicone oil with a viscosity of 5000 cP would have an approximate molecular weight of about 50,000 according to some sources.

Other polydimethylsiloxane materials include various Dow Corning® silicone fluids such as Dow Corning Medical Fluids. However, some of these materials generally have a lower viscosity and are less desirable for use herein. Dow Corning fluids with preferable physical properties include: Dow Corning 360 Medical Fluid 12,500 cSt with a reported specific gravity (density compared to water) of 0.972 at 25° C. and Dow Corning 360 Medical Fluid 1000 cSt also with a reported specific gravity (density compared to water) of 0.972 at 25° C.

Thickening Agent

The compositions of the present invention comprise from about 0.005% to about 10%, in other embodiments from about 0.0075% to about 5%, and in further embodiments from about 0.01% to about 1% by weight of a thickening agent. Suitable thickening agents herein are generally polymeric thickening agents. Some of these thickening agents can be described as hydrophilic gelling agents or can generally be described as water-soluble or colloidally water-soluble polymers, and include hyaluronic acid, carboxymethylcellulose (cellulose gum) cellulose ethers (e.g. hydroxyethyl cellulose, methyl cellulose, hydroxypropylmethyl cellulose), polyvinylpyrrolidone, polyvinylalcohol, guar gum, hydroxypropyl guar gum, and xanthan gum. Other materials include, croscarmellose sodium, which is an internally cross-linked sodium carboxymethylcellulose and alginic acid, also called algin or alginate, which is an anionic polysaccharide that can be obtained from brown algae (sea weed).

In some embodiments herein, the thickening or gelling agent used is carboxymethyl cellulose. The carboxymethyl cellulose, which can be used either in its form as supplied (non-cross-linked) or it can be cross-linked with a suitable crosslinking agent, a non-limiting example of which is 1,4,-butanediol diglycidyl ether (BDDE). In those embodiments where cross-linked carboxymethyl cellulose is desired, the cross-linking agent, i.e., the BDDE, is used at a level from 0.05% to 7% by weight, in other embodiments from 0.075% to 2% by weight, and in further embodiments at about 0.1% by weight of the composition.

Yet other thickeners or gelling materials include acrylic acid/ethyl acrylate copolymers and the carboxyvinyl polymers sold by the B. F. Goodrich Company under the trade mark of Carbopol resins. These resins consist essentially of a colloidally water-soluble polyalkenyl polyether cross-linked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are hydrophobically-modified cross-linked polymers of acrylic acid having amphipathic properties available under the Trade Name Carbopol 1382, Carbopol 1342 and Pemulen TR-1 (CTFA Designation: Acrylates/10-30 Alkyl Acrylate Crosspolymer). A combination of the polyalkenyl polyether cross-linked acrylic acid polymer and the hydrophobically modified cross-linked acrylic acid polymer is also suitable and is preferred for use herein. The gelling agents herein are particularly valuable for providing excellent stability characteristics over both normal and elevated temperatures.

In certain embodiments, the thickening agent can comprise collagen modified to dissolve in vivo within a desired timeframe (e.g., 14-36 days). For example, the collagen can partially or completely hydrolyzed to dissolve more quickly and can be crosslinked to decrease its dissolution rate.

Water

The compositions of the present invention comprise from 20% to 99%, in other embodiments from 30% to 95%, and in further embodiments from 50% to 80% water by weight. In certain embodiments of the present invention, it can be convenient to determine the water content on a volume basis. In such instances, a useful amount of water, or total aqueous solution would be about 60 mL (cc) of water to about 40 mL of the silicone oil.

Furthermore, the exact level of water in these compositions will also depend upon what other additional components are incorporated. The water used herein should be sufficiently free of impurities, pathogens, and pyrogens, and of sufficiently high purity and grade for medical use, such as a sterile injectable grade of water.

Additional Components

The compositions of the present invention can include additional components, including for example, salts, sugars, buffers, alcohols, preservatives, anti-oxidants, and UV-absorbers. The exact amounts and materials chosen can be determined by one of skill in the formulation arts to achieve a formulation with the desired characteristics.

Additional components can include solvents such as ethanol, glycerol, and propylene glycol; stabilizers such as ethylene diamine tetraacetic acid (EDTA) and citric acid; antimicrobial preservatives such as benzyl alcohol; methyl paraben, and propyl paraben; antioxidants such as butylated hydroxyanisole (BHA) and butylated hydroxytoluene (BHT); buffering agents such as citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers such as, sodium chloride, mannitol, and dextrose. The exact levels of the additional components would generally be less than about 1% by weight of the total composition, but can vary depending on the desired final composition and the target physical and physiological properties.

In other embodiments of the present invention, other additional components can include, for example those used to make a normal saline solution, which is isotonic to have an osmolality of a mammalian cell, particularly a human cell. A normal saline solution contains about 154 mmol/L of sodium ion and about 154 mmol/L of chloride ion. The compositions of the present invention can be formulated to have a final composition for the foregoing components to essentially be equivalent to a normal saline solution. Normal saline has a pH of about 5.

In yet other embodiments of the present invention, other additional components, can include, for example, those used to make Ringer's solution, particularly lactated Ringer's solution, which is isotonic with human blood, is compatible with human tissue, and is suitable for injection. Lactated Ringer's solution contains about 130 mmol/L of sodium ion, about 109 mmol/L of chloride ion, about 28 mmol/L of lactate ion, about 4 mmol/L of potassium ion, and about 1.5 mmol/L of calcium ion. The compositions of the present invention can be formulated to have a final composition for the foregoing components to essentially be equivalent to lactated Ringer's solution. Lactated Ringer's solution has a pH of about 6.5

Physical Parameters

The compositions of the present invention will generally have physical parameters that have been optimized for physical characteristics of the compositions, and the safety and efficacy of the composition.

Viscosity of the Compositions

The compositions of the present invention should have a suitable viscosity to be readily injectable using a suitable gauge syringe, typically from about 14 gauge to about 18 gauge, with an 18 gauge syringe being particularly useful. Suitable viscosities range are at least 1500 cSt, or from 1500 cSt to 20,000,000 cSt, in other embodiments from 1500 cSt to 100,000 cSt, and in further embodiments from 5,000 cSt to 30,000 cSt.

pH Range and Tonicity of the Compositions

The compositions of the present invention should have a pH and tonicity that is physiologically compatible with the tissue of the subject into which the material is to be injected, to thereby minimize discomfort and the potential for tissue damage. Suitable pH ranges are from about 4.5 to about 7. The tonicity of the compositions should generally be isotonic with human blood or human cell. A suitable target for tonicity and pH is based on the composition of a normal saline solution, as described above. Another suitable target for tonicity and pH is based on the composition of a lactated Ringer's solution, as described above.

Droplet Size

It is important that the compositions have a silicone oil droplet size within appropriate ranges, to ensure the stimulation of sufficient high quality collagen with desired properties. The compositions of the present invention are prepared to have dispersed silicone oil droplets of a desired size range. As discussed above, droplets that are either too large or too small are undesirable, and an even distribution of droplet size is preferred. The droplet size of the dispersed silicone oil droplets can be determined by microscopy and other techniques available to one of skill in the art. The droplet size can be reported as an average or mean size and can be reported with a distribution of size range. Compositions suitable for use herein have an average silicone oil diameter from 30 microns to 2000 microns, in other embodiments from 40 microns to 200 microns, and in further embodiments from 50 microns to 100 microns. In certain embodiments, the average diameter of the silicone oil droplets is greater than 100 microns.

Composition Stability and Biodegradability

The compositions of the present invention should have suitable stability, including storage stability, stability during use and injection, and stability once injected. In some embodiments it is desirable to freeze the compositions for storage. Generally, it would be desirable to have compositions that can be stored for up to about 45 days after which further FDA physical and chemical stability testing could be required. When the product is frozen, it is then thawed prior to use. The FDA generally requires that compound products be used within 72 hour of preparation or thawing.

Compositions of the invention are preferably biodegradable when implanted within a human or other lower animal. In particular, the thickening agent component of the composition is selected to degrade (e.g., dissolve) when implanted in a host, so as to allow host tissues (including nascent collagen) progressively greater access to the silicone oil droplets over time. In this way, the composition provides a temporary scaffold for collagen growth between silicon oil droplets.

The time it takes for the scaffold to dissolve can be adjusted through the selection of the thickening agent. Preferably, the scaffold dissolves in 7-70 days or 10-36 days or 14-28 days. The 14 to 28-day time frame is most preferred for penile shaft-glans-scrotal enlargement, considering that sexual activity involving physical stimulation of the enlarged regions is to be avoided until the scaffold has dissolved.

The rate of biodegradation of the thickening agent can be adjusted, e.g., through the selection of the thickening agent, adjusting the chain length of the thickening agent and adjusting the degree of crosslinking in the thickening agent. Long-lasting highly crosslinked thickening agents, such as JUVEDERM and RESTYLANE, will result in scaffolds that dissolve too slowly for penile shaft-glans-scrotal enlargement. On the other hand, if the thickening agent dissolves too rapidly, the oil droplets will coalesce and major lumps will form, there will be an increase in migration capability, and a lesser amount of overall collagen will be formed. It is preferable to form many small oil droplets surrounded by collagen rather than one large oil droplet surrounded by collagen, as the amount of collagen formed around the small oil droplets will be much more in total.

Method for Preparing the Composition

The compositions of the present invention are prepared by the following general procedure, although other embodiments are contemplated. In general, the silicone oil-in water dispersions are prepared by separately preparing the silicone phase and the water phase, and then combining these phases with appropriate mixing. The processes comprise the general steps of (i) preparing a silicone oil phase comprising the steps of:
(a) sterilizing and depyrogenizing a sample of silicone oil until essentially sterile and pyrogen-free;
(b) mixing the resultant sterile and pyrogen-free silicone oil sample with from about an equal volume to about four to five volumes of sterile injectable water, for approximately 5 minutes at about 1200 to 1500 rpm,
(c) allowing the silicone oil and water mixture to separate into two layers,
(d) removing the lower water layer and collecting the upper silicone layer (so as to remove lower molecular weight molecules produced from the manufacturing of the silicone oil and thus significantly reduce the potential chemical toxicity and/or allergic reactions from the silicone oil),
(e) repeating steps (b) through (d) on the silicone oil one or more additional times, (ii) preparing a thickened water phase comprising the steps of:
(a) dissolving a thickening agent in sterile injectable water or a sterile solution selected from normal saline, Ringer's solution, or lactated Ringers solution, solution with stirring to form a thickened water phase solution,
(b) sterilizing the thickened water phase solution,
(c) optionally freezing and thawing the sterilized thickened water phase solution,
and, (iii) preparing a silicone oil in water dispersion comprising the step of:
(a) adding approximately 40 parts by volume of the silicone oil phase to approximately 60 parts by volume of the thickened water phase with agitation to form a dispersion of the silicone oil within the water.

The above procedure can be readily modified to incorporate a crosslinking agent for the thickening agent, via the alternative for steps (a) through (c) of (ii) above, as follows with steps (a) through (d):

(ii) preparing a cross-linked thickened water phase comprising the steps of:
(a) dissolving a crosslinking agent in sterile injectable water or a sterile solution selected from normal saline, Ringer's solution, or lactated Ringers solution with stirring to form a solution of the crosslinking agent,
(b) dissolving a thickening agent in the solution of the crosslinking agent to form a thickened water phase solution,
(c) sterilizing the thickened water phase solution,
(d) optionally freezing and thawing the sterilized thickened water phase solution.

Method of Treatment

The compositions of the present invention are useful for stimulating collagen production in a mammal in need thereof, and particularly in humans. The collagen stimulation can be for a variety of medical treatments or cosmetic effects, some non-limiting examples of which include: stimulating collagen production for penile or scrotal tissue enhancement; stimulating collagen production for face or body skin wrinkle reduction; stimulating collagen production to reduce or smooth cellulite; stimulating collagen production for scar repair; or stimulating collagen production is for a hernia repair. Other nonlimiting applications include: stimulating collagen production for body or face enhancement, further exemplified by contouring the nose, ears, chin, cheeks, peri-orbital areas, forehead, drooping neck; recreation or enhancement of pectoral or abdominal musculature; buttock enhancement; filling or minimizing concave skin deformities, breast enhancement; hand rejuvenation; foot contouring—particularly thickening the bottom of the feet; intra articular joint treatments; tissue or injury repair; wound healing such as from burns or other trauma; promotion of healing and incorporation of prosthetics and implants; and inter or intra pleural treatment for conditions such as edema.

These methods for stimulating collagen involve the careful injection of the desired volume of the silicone oil-in-water emulsion into the target tissue. For such injections, typically needles or cannulas of 14 gauge to 32 gauge are used. The injection can be done subdermally or subcutaneously, with subcutaneous injection generally being preferred. The volume of the silicone oil-in-water emulsion will vary depending on the tissue to be treated and the concentration of the silicone oil in the emulsion. Some non-limiting examples of silicone oil volumes are as follows: about 5 to about 80 cc ($cm^3$ or ml), or 20-60 cc for the penile shaft, about 50 to about 150 cc for the scrotum, and about 200 to about 2000 cc for the buttocks.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Examples 1-12

In the Examples described in Table 1 below, silicone oil compositions were injected in the penile shaft of a cohort of men using the following technique.

An 18-gauge cannula was used to inject the silicone oil composition into the subcutaneous space of the penile shaft. A portal through the penile shaft skin was made by superficially poking an 18-gauge needle through the skin along the lateral mid-penile shaft area. Once the portal was made, the 18-gauge cannula was inserted through this portal and the silicone oil composition was injected into the subcutaneous space of the penile shaft. The silicone oil composition was injected through the cannula by a 10 cc syringe attached to the cannula. The syringe was detached from the cannula, reloaded with additional silicone oil composition, and reattached to the cannula for further injection as necessary to provide a desired volume of the composition in the patient.

The composition was evenly distributed along the entire subcutaneous space of the penile shaft, which includes the entire dorsal, lateral, and ventral surfaces. Considering a cannula (having a blunt tip) is used, there is substantial freedom of movement possible, because the tissue is not being cut or damaged with a sharp needle edge. It is therefore recommended that a needle not be used for the initial placement of the composition, but rather a blunt tip cannula.

After the first filler treatment and subsequent collagen formation, cannula use only is not optimal regarding filler placement and clinical results. After the first filler treatment, this newly formed collagen layering will no longer allow for total freedom of movement by a cannula due to the fundamental architectural change that has occurred under the penile skin, or in the subcutaneous space. This new collagen formation causes an increase in tissue density which will now hinder a blunt tipped instrument (cannula) to penetrate appropriately and efficiently. So now that this newly formed collagen occupies this space, the ability to move the cannula around freely becomes limited. Therefore, a combination cannula and needle technique is preferred for all subsequent treatments. This new layer of collagen present in the subcutaneous space, after the first penile enlargement procedure, is most effectively penetrated and filled by using a needle and additional force.

It is most preferred to use a 1-cc syringe with an attached 25 g needle so as to provide the positional mechanism (needle) and the force (1-cc syringe) necessary to deposit the filler composition into place. For example, the needle can easily be positioned into the collagen space with minimal effort. The 1-cc syringe will provide the force by which to deliver the syringe contents. Larger syringes will provide lesser amounts of force per unit area, and are therefore less preferred. The 1-cc syringe with the small gauge needle yields superior enlargement and symmetrical results, particularly when used for treatments subsequent to the initial treatment with the first collagen layering.

A cannula is less preferred in such circumstances, because the blunt tip will not readily penetrate the new dense collagen formation. In addition, the needle technique can also deposit filler directly above, within and below the newly formed collagen with precision and with precise quantities, which a cannula cannot easily do. Using only a cannula at this stage would result in a higher risk of asymmetric placement and thus asymmetric results (lumpy formation and clinically not acceptable). When using the appropriate combination technique, a cannula and syringe, the free space that is available can be addressed by the cannula, and the denser collagen zones can be addressed by the needle.

After placement of the composition, a substantial effort was made to mold and shape the composition into place by manual, finger and hand pressure and manipulation. The application of pressure and manipulation is important to ensure that the distribution of the composition is even. If this manipulation is not done, major lumpy and asymmetric collagen areas can develop.

In the following examples, flaccid state measurements (flaccid measurements) of penile girth were taken prior to and following injection into the penis shaft of 35-40 cc of a filler composition. The compositions are shown in Table 1 below. The results are shown in Tables 2 and 3 below. Erect state values were estimated to be 25% greater than the flaccid state measurements.

TABLE 1

Silicone Oil Compositions

| Example | Ingredient | Amount (weight %) |
|---|---|---|
| 1 | Silicone Oil (1000 cSt viscosity) | 40% |
|   | Low level cross-linked Hyaluronic Acid (HA) | 2% |
|   | Sterile Water for Injection | Approximately 58% (QS to make 100%) |
| 2 | Silicone Oil (1000 cSt viscosity) | 20% |
|   | Low level cross-linked HA | 2% |
|   | Sterile Water for Injection | Approximately 78% (QS to make 100%) |
| 3 | ADATO-SIL 5000 (5000 cSt viscosity) | 40% |
|   | Low level cross-linked HA | 2% |
|   | Sterile Water for Injection | Approximately 58% (QS to make 100%) |
| 4 | ADATO-SIL 5000 (5000 cSt viscosity) | 20% |
|   | Low level cross-linked HA | 2% |
|   | Sterile Water for Injection | Approximately 78% (QS to make 100%) |
| 5 | ADATO-SIL 5000 (5000 cSt viscosity) | 40% |
|   | Non-Crosslinked Carboxymethylcellulose (CMC) | 2% |
|   | Sterile Water for Injection | Approximately 58% (QS to make 100%) |
| 6 | ADATO-SIL 5000 (5000 cSt viscosity) | 20% |
|   | Non-Crosslinked CMC | 2% |
|   | Sterile Water for Injection | Approximately 78% (QS to make 100%) |
| 7 | Silicone Oil (12500 cSt viscosity) | 40% |
|   | Non-Crosslinked CMC | 2% |
|   | Sterile Water for Injection | Approximately 58% (QS to make 100%) |
| 8 | Silicone Oil (12500 cSt viscosity) | 20% |
|   | Non-Crosslinked CMC | 2% |
|   | Sterile Water for Injection | Approximately 78% (QS to make 100%) |
| 9 | Silicone Oil (12500 cSt viscosity) | 40% |
|   | Lactated Ringers Solution | 29% |
|   | Non-Crosslinked CMC | 2% |
|   | Sterile Water for Injection | Approximately 29% (QS to make 100%) |
| 10 | Silicone Oil (12500 cSt viscosity) | 20% |
|   | Lactated Ringers Solution | 29% |
|   | Non-Crosslinked CMC | 2% |
|   | Sterile Water for Injection | Approximately 49% (QS to make 100%) |
| 11 | Silicone Oil (12500 cSt viscosity) | 40% |
|   | Lactated Ringers Solution | 29% |
|   | Low-level Crosslinked CMC | 2% |
|   | 1,4-Butanediol Diglycidyl Ether (BDDE) | 0.1% |
|   | Sterile Water for Injection | Approximately 29% (QS to make 100%) |
| 12 | Silicone Oil (12500 cSt viscosity) | 20% |
|   | Lactated Ringers Solution | 29% |
|   | Low-level Crosslinked CMC | 2% |
|   | 1,4-Butanediol Diglycidyl Ether (BDDE) | 0.1% |
|   | Sterile Water for Injection | Approximately 49% (QS to make 100%) |

TABLE 2

Quantitative Results

| Example | Oil Viscosity (cSt) | Thickener | Cross-linking of Thickener | Pre-Treatment Girth (cm) Flaccid | Pre-Treatment Girth (cm) Erect | Post-Treatment Girth (cm) Flaccid | Post-Treatment Girth (cm) Erect |
|---|---|---|---|---|---|---|---|
| 1 | 1000 | HA | Low | 9.5 | 11.4 | 11.4 | 13.3 |
| 2 | 1000 | HA | Low | 9.5 | 11.4 | 10.8 | 12.7 |
| 3 | 5000 | HA | Low | 10 | 12.7 | 12 | 14.6 |
| 4 | 5000 | HA | Low | 9 | 10.8 | 10 | 12 |
| 5 | 5000 | CMC | None | 9.5 | 11.4 | 10.5 | 13.3 |
| 6 | 5000 | CMC | None | 10.8 | 13.3 | 12 | 14.6 |
| 7 | 12500 | CMC | None | 10 | 12.7 | 12.7 | 15.2 |
| 8 | 12500 | CMC | None | 10 | 12.7 | 12 | 14.6 |
| 9 | 12500 | CMC | None | 9.5 | 11.4 | 12 | 14 |
| 10 | 12500 | CMC | None | 9 | 10.8 | 10.8 | 12.7 |
| 11 | 12500 | CMC | Low | 9 | 10.8 | 10.5 | 13.3 |
| 12 | 12500 | CMC | Low | 10 | 12.7 | 12 | 14.6 |

TABLE 3

Qualitative Results

| Example | Incidence of Palpable Lumps on Shaft | Migration (Incidence of Palpable Lumps on Pubic or Scrotal Areas) | Incidence of Skin Ulceration or Irritation | Girth Gain |
|---|---|---|---|---|
| 1 | High | High | High | Good |
| 2 | High | High | Moderate | Fair to Good |
| 3 | Low to Moderate | Low to Moderate | Low | Good |
| 4 | Low to Moderate | Low to Moderate | Very Low | Fair to Good |
| 5 | Low to Moderate | Low to Moderate | Low | Good |
| 6 | Low to Moderate | Low to Moderate | Very Low | Fair to Good |
| 7 | Very Low | Very Low | Very Low | Very Good |
| 8 | Very Low | Very Low | Very Low | Good |
| 9 | Very Low | Very Low | Very Low | Very Good |
| 10 | Very Low | Very Low | Very Low | Good |
| 11 | Rare | Rare | Rare | Very Good |
| 12 | Rare | Rare | Rare | Very Good |

The data show that oils with increasing viscosities provided better clinical results with fewer side effects. More specifically, the trends observed using high viscosity 12500 cSt oil resulted in rare incidences of lumpiness (oil coalescence) and migration of the oil. Oils with high viscosity have reduced oil droplet coalescence, which prevents the formation of larger oil droplets and lumps, and significantly reduces the risk of migration.

The data also show that low level crosslinking of the thickener yields better results than non-crosslinked thickener. The best results were seen using a combination of high viscosity oil with a low level crosslinked thickener. CMC is inherently more difficult to break down by the human body than HA (5-7 days vs. 48-72 hours respectively). Thus, non-crosslinked CMC is preferable to non-crosslinked HA, but low cross-linked CMC is preferable to both.

While not tested, it is expected that the use of non-cross linked HA would yield unacceptable clinical results due to prematurely dissolving, resulting in the increased risk of oil coalescence, lumpy formation, and greater migration into the pubic and scrotal areas.

Highly crosslinked HA (e.g., as found in commercial products such as JUVEDERM and RESTYLANE) would be expected to dissolve too slowly to provide scaffolding for collagen growth in a reasonable time frame. This is particularly problematic for the penile enlargement patient for several reasons.

First, the patient will not wait up to 1.5 years for the collagen to be produced before resuming intercourse. Engaging in sexual intercourse before the collagen has completely formed will physically push the unconverted non-stable mixture into the pubic and or scrotal areas. Highly crosslinked HA will unduly delay collagen formation, which will result in delaying the anchoring of collagen to the surrounding tissues causing instability and mobility of filler during physical duress.

Second, there is a high risk of imbalance and asymmetrical shape development due to long-term collagen production with an organ that expands, contracts, bends, etc., on a daily basis, increasing the shifting and movement of the filler material which in turn increases the risk of misshaping.

In addition, the use of a longer acting filler, such as JUVEDERM, in the volumes necessary for appreciable augmentation of the penile shaft, glans and/or scrotal areas, would result in an extended opportunity for large amounts of filler to migrate before being anchored by collagen formation. The risk of such longer acting fillers migrating into the pubic and or scrotal areas would be unacceptably high, essentially precluding the use of such fillers in large volumes. While it is theoretically possible to reduce the risk of large volume filler migration by injecting lesser amounts of longer acting fillers over an extended period of time, the number of procedures necessary to achieve an appreciable augmentation makes this method of treatment impractical and unappealing to patients.

The above composition and method variants of this example demonstrate that the compositions and methods of the present invention are useful for stimulating collagen production for male enhancement. The compositions and methods of the present invention are also useful for, e.g., stimulating collagen production for face or body skin wrinkle reduction, smoothing cellulite, scar repair, hernia repair, and breast enhancement.

While the invention has been described in detail and with reference to specific examples thereof, it will be apparent to one skilled in the art that various changes and modifications can be made therein without departing from the spirit and scope thereof.

What is claimed is:
1. A filler composition comprising:
   (a) 1% to 80% of a silicone oil having a viscosity from 12500-30000 centistokes (cSt);
   (b) 20% to 99% of water; and
   (c) 0.005% to 10% of a thickening agent,
   wherein the filler composition is a pharmaceutically acceptable oil-in-water emulsion, the silicone oil is dispersed in the water as droplets having an average diameter from 30 microns to 2000 microns and the thickening agent is sufficiently biodegradable when implanted subcutaneously in a human to provide a temporary scaffold for collagen growth between silicone oil droplets.

2. The filler composition of claim 1, wherein the thickening agent when implanted subcutaneously is sufficiently biodegradable such that the temporary scaffold dissolves in 14-28 days.

3. The filler composition according to claim 1, wherein the average diameter of the droplets is greater than 100 microns.

4. The filler composition according to claim 1, wherein the thickening agent is a member selected from the group consisting of carboxymethyl cellulose, poly(ethylene oxide), poly(propylene oxide), collagen and mixtures thereof.

5. The filler composition according to claim 1, wherein the thickening agent is carboxymethyl cellulose.

6. The filler composition according to claim 1, wherein the thickening agent is carboxymethyl cellulose or hyaluronic acid, and the thickening agent is cross-linked with 1,4-butanediol diglycidyl ether in an amount from 0.05% to 7% based on a weight of the thickening agent.

7. The filler composition according to claim 1, wherein the thickening agent is hyaluronic acid cross-linked with a degree of modification of 0.1 to 0.9.

8. The filler composition according to claim 1, wherein the filler composition has a viscosity of 12500 cSt to 20,000,000 cSt.

9. The filler composition according to claim 1, wherein the silicone oil comprises at least one member selected from the group consisting of polydimethylsiloxane, fluorinated polysiloxanes, dimethiconol and silicone polyethers.

10. The filler composition according to claim 1, wherein the silicone oil comprises polydimethylsiloxane with a viscosity of 12500 cSt.

11. The filler composition according to claim 1, wherein the silicone oil constitutes 20% to 50% of the filler composition.

12. The filler composition according to claim 1, wherein the water constitutes 50% to 80% of the filler composition.

13. The filler composition according to claim 1, wherein the thickening agent constitutes 0.01% to 1% of the filler composition.

14. The filler composition according to claim 1 further comprising at least one ion selected from the group consisting of:
   up to 154 mmol/L of sodium ion;
   up to 154 mmol/L of chloride ion;
   up to 28 mmol/L of lactate ion;
   up to 4 mmol/L of potassium ion; and
   up to 1.5 mmol/L of calcium ion.

15. The filler composition according to claim 1, which is effective to stimulate formation of a collagen matrix which anchors the silicone oil droplets in place as the temporary scaffold dissolves.

16. A method for preparing the filler composition according to claim 1, comprising the steps of:
   preparing a silicone oil phase comprising the steps of:
      (a) providing a silicone oil that is substantially sterile and substantially free of pyrogen;
      (b) mixing the silicone oil with 1-5 volumes of sterile injectable water for 4 to 6 minutes at 1200 to 1500 rpm;
      (c) allowing the silicone oil and water mixture to separate into a lower water layer and an upper silicone layer;
      (d) removing the lower water layer and collecting the upper silicone layer; and
      (e) repeating steps (b) through (d) on the silicone oil at least once to obtain the silicone oil phase;
   (ii) preparing a thickened water phase solution comprising the steps of:
      (a) dissolving with stirring a thickening agent in a sterile solvent selected from the group consisting of injectable water, normal saline, Ringer's solution, and lactated Ringer's solution, to form a thickened water phase solution;
      (b) sterilizing the thickened water phase solution; and
      (c) optionally freezing and thawing the sterilized thickened water phase solution; and
   (iii) preparing a silicone oil-in-water emulsion by combining 35-45 parts by volume of the silicone oil phase with 55-65 parts by volume of the thickened water phase solution with agitation to form an emulsion of the silicone oil within the water.

17. The method of claim 16, wherein the sterile solvent contains a cross-linking agent which forms cross-links in the thickening agent.

18. The method of claim 17, wherein the cross-linking agent is 1,4-butanediol diglycidyl ether in an amount from 0.05% to 7% based on a weight of the thickening agent.

19. A soft tissue augmentation method comprising subcutaneously injecting into a patient the filler composition of claim 1.

20. The soft tissue augmentation method of claim 19, wherein a volume of 20 to 60 ml is injected into a single injection site in a single treatment.

21. The soft tissue augmentation method of claim 19, wherein:
   the filler composition stimulates collagen growth;
   the thickening agent forms a temporary scaffold for collagen growth between silicone oil droplets; and
   a collagen matrix anchors the silicone oil droplets in place as the temporary scaffold dissolves within 14-28 days.

22. The soft tissue augmentation method of claim 19, wherein the filler composition is injected into a penis or a scrotum for penis or scrotum enhancement.

23. The soft tissue augmentation method of claim 19, wherein a wrinkle or depression on the face or body is filled with the filler composition.

24. The soft tissue augmentation method of claim 19, wherein a scar is repaired.

25. The soft tissue augmentation method of claim 19, wherein a hernia is repaired.

26. The soft tissue augmentation method of claim 19, wherein the filler composition is injected into a breast for breast enhancement.

* * * * *